(12) United States Patent
Schuller

(10) Patent No.: US 11,007,341 B2
(45) Date of Patent: May 18, 2021

(54) AIR PURIFIER APPARATUS

(71) Applicant: Carmen Schuller, Mooresville, NC (US)

(72) Inventor: Carmen Schuller, Mooresville, NC (US)

(73) Assignee: Carmen Schuller, Mooresville, NC (US)

( * ) Notice: Subject to any disclaimer, the term of this patent is extended or adjusted under 35 U.S.C. 154(b) by 675 days.

(21) Appl. No.: 15/197,152

(22) Filed: Jun. 29, 2016

(65) Prior Publication Data

US 2018/0001049 A1  Jan. 4, 2018

(51) Int. Cl.
*A61M 16/10* (2006.01)
*B01D 53/04* (2006.01)
(Continued)

(52) U.S. Cl.
CPC ...... *A61M 16/105* (2013.01); *A61M 16/0066* (2013.01); *A61M 16/021* (2017.08); *A61M 16/06* (2013.01); *A61M 16/101* (2014.02); *A61M 16/107* (2014.02); *A61M 16/1055* (2013.01); *A61M 16/1075* (2013.01); *A62B 7/02* (2013.01); *A62B 7/08* (2013.01); *A62B 7/10* (2013.01); *A62B 18/025* (2013.01); *B01D 53/0415* (2013.01); *B01D 53/0454* (2013.01); *A61M 16/16* (2013.01); *A61M 2016/1025* (2013.01); *A61M 2205/0205* (2013.01);
(Continued)

(58) Field of Classification Search
CPC ............ B01D 53/0415; B01D 53/0454; B01D 2259/4541; B01D 2259/4533; B01D 2259/455; A62B 18/025; A62B 18/006; A62B 7/02; A62B 7/10; A62B 7/08; A62B 9/006; A62B 23/02; A61M 2205/8206; A61M 2205/507; A61M 16/0066; A61M 16/021; A61M 16/06; A61M 16/105; A61M 16/1055; A61M 16/10

See application file for complete search history.

(56) References Cited

U.S. PATENT DOCUMENTS 3,139,327 A * 6/1964 Marshall ............. C01B 15/0435
423/641
4,233,972 A   11/1980 Hauff et al.
(Continued)

FOREIGN PATENT DOCUMENTS

CN   201510320872 A   6/2015
CN   201510320874 A   6/2015

OTHER PUBLICATIONS

Sundberg, Jonas; Cameron, Lisa J.; Southon, Peter D.; Kepert, Cameron J.; McKenzie, Christine J. (2014). "Oxygen chemisorption/desorption in a reversible single-crystal-to-single-crystal transformation" Chem. Sci., 2014,5, 4017-4025.

*Primary Examiner* — Kendra D Carter
*Assistant Examiner* — Brian T Khong
(74) *Attorney, Agent, or Firm* — Leason Ellis LLP

(57) ABSTRACT

The invention relates to a modular, portable, air purifier device capable of supplying filtered or otherwise conditioned airflow to an individual. More specifically, the present invention provides an air purification system that allows for the remote detection and analysis of local ambient air quality and transmit that information to wirelessly connected devices.

10 Claims, 7 Drawing Sheets

(51) Int. Cl.
*A61M 16/00* (2006.01)
*A61M 16/06* (2006.01)
*A62B 7/08* (2006.01)
*A62B 7/02* (2006.01)
*A62B 7/10* (2006.01)
*A62B 18/02* (2006.01)
*A61M 16/16* (2006.01)
*B01D 53/047* (2006.01)

(52) U.S. Cl.
CPC .......... A61M 2205/053 (2013.01); A61M 2205/3368 (2013.01); A61M 2205/3653 (2013.01); A61M 2205/50 (2013.01); A61M 2205/8206 (2013.01); A61M 2209/088 (2013.01); A61M 2210/0618 (2013.01); B01D 53/047 (2013.01); B01D 2253/102 (2013.01); B01D 2253/108 (2013.01); B01D 2256/12 (2013.01); B01D 2257/106 (2013.01); B01D 2257/90 (2013.01); B01D 2259/40088 (2013.01); B01D 2259/4533 (2013.01); B01D 2259/4541 (2013.01)

(56) References Cited

U.S. PATENT DOCUMENTS

| | | | |
|---|---|---|---|
| 4,238,464 A * | 12/1980 | Gustafson | C01B 15/00 252/186.22 |
| 4,331,141 A | 5/1982 | Pokhis | |
| 4,363,322 A * | 12/1982 | Andersson | A61F 13/00029 604/359 |
| 4,622,963 A * | 11/1986 | Ansite | A61M 16/00 128/203.27 |
| 4,651,731 A * | 3/1987 | Vicenzi | A61M 16/00 128/204.25 |
| 5,009,225 A | 4/1991 | Vrabel | |
| 5,267,557 A | 12/1993 | Her-Mou | |
| 5,848,592 A | 12/1998 | Sibley | |
| 5,878,742 A | 3/1999 | Figueredo et al. | |
| 6,772,762 B2 | 8/2004 | Piesinger | |
| 7,748,380 B1 * | 7/2010 | Phifer | A62B 7/02 128/201.25 |
| 2004/0005252 A1 * | 1/2004 | Siess | B01D 53/34 422/186.3 |
| 2005/0103343 A1 * | 5/2005 | Gosweiler | A62B 18/006 128/206.12 |
| 2005/0268916 A1 * | 12/2005 | Mumford | A61M 16/06 128/207.13 |
| 2006/0048777 A1 * | 3/2006 | Brookman | A62B 7/02 128/201.22 |
| 2009/0266361 A1 * | 10/2009 | Bilger | A62B 7/10 128/204.21 |
| 2010/0052293 A1 * | 3/2010 | Brooks | A61M 16/101 280/651 |
| 2010/0116270 A1 * | 5/2010 | Edwards | A61M 16/0833 128/201.21 |
| 2010/0263664 A1 * | 10/2010 | Radivojevic | A61M 16/0677 128/202.26 |
| 2012/0167879 A1 * | 7/2012 | Bowman | A61M 16/0066 128/201.22 |
| 2013/0037027 A1 * | 2/2013 | Schuller | A62B 18/08 128/204.21 |
| 2013/0192596 A1 * | 8/2013 | Rittner | A62B 21/00 128/202.26 |
| 2013/0312745 A1 * | 11/2013 | Kshirsagar | A62B 18/02 128/202.26 |
| 2014/0000594 A1 * | 1/2014 | Rittner | A62B 9/02 128/202.26 |
| 2014/0005497 A1 * | 1/2014 | Larsen | A61B 5/6803 600/301 |
| 2014/0041662 A1 * | 2/2014 | Almqvist | A61M 16/06 128/204.23 |
| 2014/0182586 A1 * | 7/2014 | Glazier | A61M 16/021 128/202.26 |
| 2014/0224126 A1 * | 8/2014 | Whitcher | B01D 53/0415 96/121 |
| 2014/0248195 A1 * | 9/2014 | Vigier | A62B 7/08 422/240 |
| 2014/0366873 A1 * | 12/2014 | Robey | A62B 7/00 128/201.22 |
| 2014/0373846 A1 * | 12/2014 | Kao | A62B 7/10 128/204.23 |
| 2015/0283409 A1 * | 10/2015 | Buck | A62B 7/02 128/204.22 |
| 2016/0089552 A1 * | 3/2016 | Murray | A62B 9/006 128/202.22 |
| 2016/0270656 A1 * | 9/2016 | Samec | A61B 3/085 |
| 2016/0339202 A1 * | 11/2016 | Burchell | A61M 16/04 |
| 2016/0355262 A1 * | 12/2016 | Sharma | A62B 7/14 |
| 2017/0072231 A1 * | 3/2017 | Carr | A62B 9/006 |
| 2017/0315359 A1 * | 11/2017 | Grashow | G02B 27/017 |
| 2017/0361133 A1 * | 12/2017 | Yu | F04D 25/084 |
| 2018/0326231 A1 * | 11/2018 | Boomgaarden | A62B 7/08 |

\* cited by examiner

AIR PURIFIER APPARATUS

This application claims priority in part to U.S. application Ser. No. 15/144,540. This invention relates to a portable wearable powered oxygen and air generation, filtration, conditioning, and sterilization system.

BACKGROUND OF THE INVENTION

Devices for respiratory protection are readily available for medical applications. The most common devices are negative pressure respirators which typically take the form of either a mask or a half mask respirator. In either case, the mask covers the nose and mouth and air is drawn through the filter by the negative pressure of inhalation. These types of masks increase respiratory stress because the user must overcome the air restriction presented by the air filter. A tight fit is essential to prevent unfiltered air from entering around the mask instead of through the filter. These types of masks also interfere with normal conversation because they cover both the nose and mouth.

Also available, are Powered Air Purifying Respirators (PAPRs) which use small battery operated motor and fan assemblies to draw air through the filter and supply it at a positive pressure to the user's face mask. These units eliminate respiratory stress and are not dependent on a tight fit between the face and mask. However, they also interfere with normal conversation because they are supplied with full or half masks that cover both the nose and mouth.

The problem with both these types of respirators is that they are not cosmetically appealing and are therefore seldom worn outside an industrial workplace. For example, those devices in the prior art, are not portable or unobtrusive enough to be suitable. U.S. Pat. No. 5,267,557 to Her-Mou herein incorporated by reference, is directed to providing a nose mask with a filtering device and nose clamp. The mask has been adapted to have an inlet pipe and an exhaust pipe and the air supply being driven by a dc current motor. U.S. Pat. No. 4,233,972 to Hauff herein incorporated by reference, is directed to providing a battery operated filter blower unit arranged to be supported by the person. The mask has a filter unit and blower unit that can be adapted to different types of face masks. The filtered blower also has an ejection space for the diffusion of blown air. U.S. Pat. No. 4,331,141 to Pokhis; U.S. Pat. No. 5,009,225 Vrabel; U.S. Pat. No. 5,848,592 Sibley; U.S. Pat. No. 6,772,762 Piesinger, all of which are herein incorporated by reference, provides a head and upper torso covering devices wherein upon inhalation, air from the ambient surroundings are drawn in through a filter and passed to the user. Additionally, the inventions optionally provide for electric motors to impel air into the apparatus.

However, there are many non-industrial situations in which respiratory protection would be highly beneficial. Allergy sufferers would greatly benefit from a pollen filter when outside during the allergy season as would people bothered by air pollution on high pollution days. Airline travelers would benefit from a cabin air ozone and germicidal filter, especially on long flights. Hospital workers and patients would benefit from germicidal filters. Finally, industrial workers would benefit from a less obtrusive respirator in non-toxic environments such as woodworking.

Although negative respirators could be worn in everyday non-industrial environments, they seldom are because of their obtrusiveness, respiratory discomfort, and difficulty in engaging in conversation. Currently available positive pressure PAPRs are large, noisy, and typically are supplied with full face masks. It would be extremely rare to see one of these units worn outside the workplace.

In summary, there are currently no acceptable devices for respiratory protection that are practical and cosmetically acceptable for use outside the industrial environment.

Figuereo, et al in U.S. Pat. No. 5,878,742, herein incorporated by reference, attempts to make a PAPR more appealing by disclosing a plenum go arrangement near the forehead of the wearer along with a baffle for distributing the air from the plenum downward over the wearer's mouth, nose, and face. However, his device is still very large and obtrusive and would not appeal to users outside the workplace.

The primary problem with current portable PAPRs is that they are powered by fans or blowers. Fans and blowers can only supply very low static air pressures. This requires that large diameter hoses and large surface area air filters be used so as to not overly constrict the airflow from the blower. Typical hose diameters between a belt mounted blower and the face mask are one inch or larger.

Another problem with current negative respirators and PAPRs is that they are all designed to cover both the nose and mouth. However, covering only the nose would be perfectly acceptable in many non-toxic environments. For example, an allergy sufferer breathing filtered air through the nose would not be bothered by an occasional breath of unfiltered air through the mouth.

Yet another problem with both negative respirators and PAPRs is that they are only designed to filter the air and not to sterilize or condition it.

Accordingly, it is the object of the present invention to provide a new personal positive pressure powered respiratory protection system that would be cosmetically acceptable to the average user in an everyday environment.

Another object of the invention is to provide a system that can be easily configured for different filtering situations by offering various types of air filtration, sterilization, and conditioning capabilities using standard plug-in modules. Typical types of air filtration that will be provided are particulate, odor, ozone, and selected organic and chemical vapors. Sterilization will be provided using ultra-violet germicidal lamps. Typical air conditioning provided will be heating, cooling, or moisturizing the filtered air.

Yet another object of the invention is to make the whole system portable, wearable, and concealable.

SUMMARY OF THE INVENTION

In accordance with the broad aspects of the present invention, the apparatus disclosed provides a portable air purifier capable of supplying filtered or otherwise conditioned airflow to an individual. More specifically, the present apparatus provides, in part, a modular air purification system that allows for the selection of air treatment modules and the combining of them to achieve desired air quality and characteristics.

The present device allows an individual to filter the ambient atmosphere in a way that is unobtrusive and does not require extensive machinery. Additionally, the present device is compact and easily portable, allowing for ease of movement.

A further aspect of the apparatus allows a user to filter smoke, dust and other allergens so as to enable a healthier environment for those persons who are sick or of advanced illness. In the present invention, the air purifier and its connected nasal mask are light enough to be carried or worn on a variety of transportation mediums, such as airplanes, trains, and in extended car travel.

A still further aspect of the apparatus allows for the modular system to be customizable for various tasks such as air purification, sterilization, and conditioning configurations by simply plugging in different filter, conditioning or sterilization modules.

BRIEF DESCRIPTION OF THE DRAWINGS

The foregoing and other features of the present invention will be more readily apparent from the following detailed description and drawings of illustrative embodiments of the invention in which list the drawings and their captions.

DETAILED DESCRIPTION OF THE INVENTION

By way of overview and introduction, the present invention concerns an apparatus for generating a purified air for personal, intimate use by an individual. The apparatus is further directed to modular personal air purifier system that is portable and discrete. Lastly, the present invention allows for a device that provides sufficient air pressure which employs the use of minimal electrical power to effectuate itself.

Figure 1:
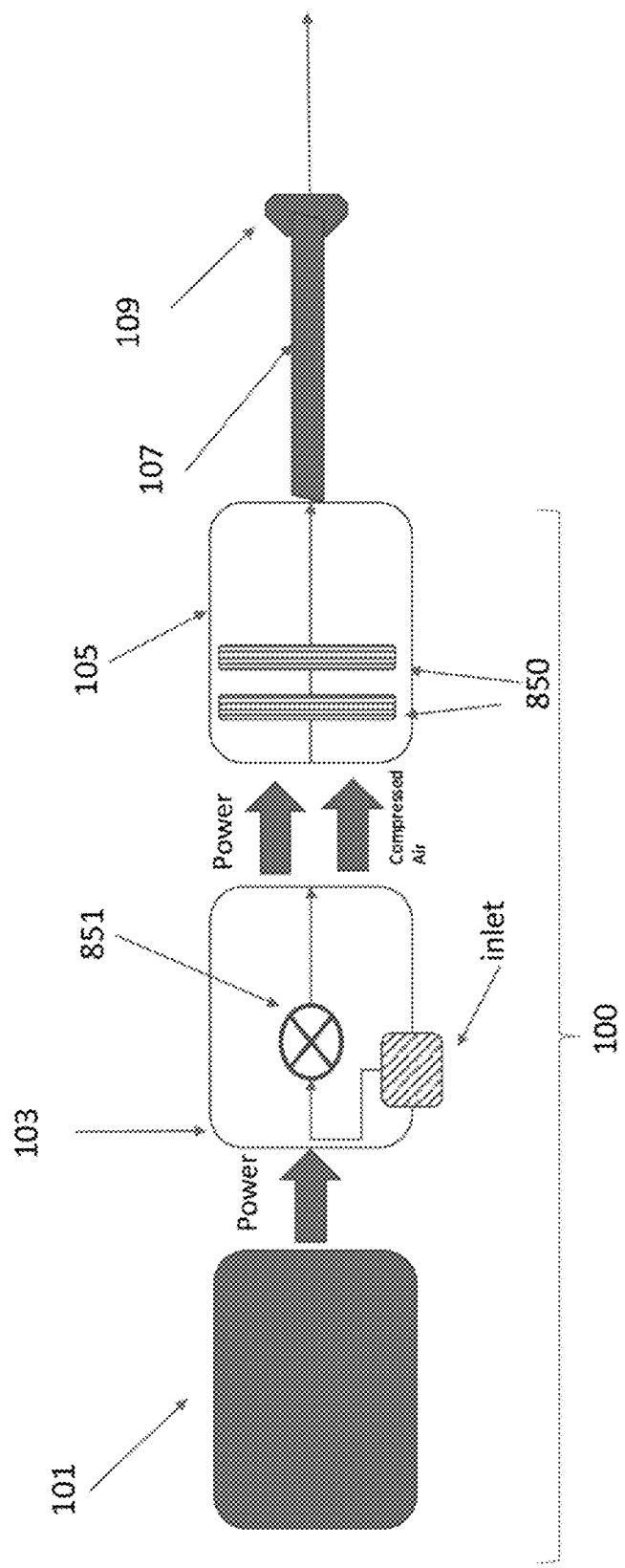
FIG. 1 is an illustrative side diagram of the components of an embodiment of the invention.

As seen in FIG. 1, the present invention provides a modular air purifier 100. The air purifier apparatus is configured to have a series of discrete physical modules that are configured to fit to one another (101,103,105) so as to provide all the necessary functions of a portable air purifier. In one embodiment of the device, a power pack 101 is secured to an air compression module 103. The power pack is configured as a housing, having a body of roughly cylindrical or oblong dimensions. Within this housing, an electrical energy generation means is secured, for example a battery pack. Furthermore, the power module is configured so that all necessary electrical connections are made between the air compression module 103 and the power module 101 without the need additional tools or hardware. In an embodiment of the apparatus shown, the power module 101 is provided with a series of batteries (not shown). The provided batteries are rechargeable and removable from the power module 101. In another configuration, the power module itself is rechargeable by connecting it to a power source, such as an electrical outlet, charging cable, or charging dock. In one or more implementations, the charging dock uses wireless charging elements incorporated into the power module 101 and a base station to charge the all or a portion of the power module 101.

Additionally, in an alternative embodiment, the power module 101 can supply direct current from a residential outlet or commercial source by employing an AC/DC converter. In an alternative embodiment, the present invention power module uses a fuel cell or other form of electrical energy generation. Additionally, in still a further embodiment, a photovoltaic cell is affixed to the body and provides either supplemental, or compete electrical power to the device. In still a further embodiment, an airplane or automobile charger can supply direct electrical power to the power module 101.

The power module 101 is fitted via electrical and physical connectors to an air compression module 103. The air compression module 103 is configured to extract ambient air from the surrounding environment via vents and direct it to the user via a hose or tubing 107 to a nasal cover 109. The air compression module 103 is configured as being located within a housing of similar dimensions to that of the power pack. Those skilled in the art would readily appreciate that the dimensions described herein are in no way limited.

The present device is configured as an air compressor that is designed to function utilizing the low current and voltage supplies of batteries and other direct current power sources. The air compressor may be a custom or commercial available compressor suitable for the functions so described. Furthermore, those skilled in the art would easily recognize any necessary gearing, valves, and other air movement elements necessary for a functioning air compressor so as to be fully described. The electrical connections that provide linkages to the power module are provided within the body of the housing and are configured to direct electricity to the internal mechanism of the air compressor, for example, a brushless motor. In the provided embodiment, the air compressor module is configured to use a standard fan-bladed compressor (851) to compress air. This air is extracted through vent openings located on the sides of the air compressor housing 103. Once air has been compressed, it is directed to the front of the device, through another vent or grate.

An alternative embodiment provides that present device employs the use of blade-less fans or air compression devices, such as impellers. In a still further embodiment of the device, the air compressor can use a bladed intake fan along with induced effects from an impeller using the Coanda effect. For example, by the generation of low pressure zones around a vent and hence inducing air flow that lacks buffeting. Therefore, in those embodiments incorporating this type of air compressor, the resulting air stream is less volatile and provides for a gentler inhalation experience.

As stated previously, the body of the air compressor module can be made in similar dimensions and materials as the power unit 101. However, in the present embodiment the overall length of the air compression module 103 is larger than that of the power module 101. Those skilled in the art would rapidly recognize those materials and housing elements that would suitably allow for the durable construction of an air compressor, such as steel, plastics, composites and synthetic materials.

As in the embodiment of the device depicted in FIG. 1, once the air has been compressed by in the air compression module 103, the compressed air is directed to a filtering unit 105. The filtering unit 105 is configured as a modular housing having the same size and shape as the previous modules. The body of the housing posses a vent that accepts the compressed air from the air compression unit 103 and passes it through a series of removable or non-removable filters (850). These filters can be of any type and made suitable to restrain particulate matter in the air stream. For example it is provides that the filters can remove, dust, pollen and other allergens from the air prior to inhalation by the user. Additionally, it is possible to use electrostatic filters to remove particles, such as smoke, from the air stream. Additionally, filters with anti-bacterial, anti-microbial or anti-viral properties can be included. In an additional embodiment, the filters of the present device also include a series of filters that can be stacked so as to achieve combination of filtering mechanisms. In accordance with the outlines of the invention, it is possible to effectuate air filtering using a series of filters. For example particulate filtering provided using HEPA (high efficiency particulate air) filters. Odor and ozone filtering will be provided using activated carbon, cpz (carbon, permanganate, and zeolite), or the like. Organic and chemical vapor filtering could be provided using readily available filters custom packaged for this system. Air sterilization will be provided using an ultraviolet germicidal lamp. Air conditioning will be provided using a distilled water moisturizing module for humidifying, a solid state thermoelectric cooler module for cooling, and a resistive element for heating.

Upon filtering of the air stream, the filter module 105 directs the filtered air to a progressively narrowing cap 104 that increases the air pressure and drives the compressed air through a flexible tube 107 or conduit.

The filtered air, directed through the tube 107, is then transported to the nasal mask 109. The nasal mask 109 is configured and adapted to cover the nose of the user, but does not interfere with the mouth or eyes of the user. The nasal mask 109 is configured with an inlet that allows the tube to direct filtered and compressed air to the nose. In a particular embodiment, the nasal mask 109 is secured to the face of the user with a strap or string that wraps around the back of the skull and is secured with a clasp or tab. In an alternative embodiment, the pressed device uses negative pressure to secure the nasal mask to the face without the need of straps. In this embodiment, the nasal mask 109, or the nose and face mask 202 of FIG. 4 contains vents 301 on its surface that are capable of opening outwards only. As such when a user exhales, the vents open and expel the user's breath. Alternatively, when the user inhales, the vents are closed, thereby producing negative pressure, which accelerates the filtered air into the user's lungs, as well as forming an air tight seal with the nasal mask.

In a further embodiment of the present invention, the air purifier device includes a mask 202 configured to cover the nose and the mouth of the user. In one or more embodiments, the mask 202 is equipped with a gasket or other material suitable for forming an air-tight seal with the face of a user. In a further embodiment, the mask is equipped with a material hood configured to be passed over the user's head and encase the users head, with the exception of the user's eyes, nose, and mount in a anti-bacterial or contaminant resistant covering. For example, a balaclava style covering, designed to expose only a portion of the user's face, is integrated with the mask.

In another embodiment, the mask 202 is equipped with a device or mechanism for securing the mask to the user's face. For example, a strap or band is affixed to the mask 202 and fits around the user's head. In yet an alternative arrangement, the mask 202 is fixed to the user's face through surface tension or suction. For example, the mask 202 is configured with a plurality of suction devices around the perimeter of the mask that affix to the face of the user and are designed to secure the mask to the user's face. In a further arrangement, the interior surface of the mask is coated or formed of an antimicrobial or anti-biological agent.

The mask 202, in one embodiment, is equipped with one or more sensors 660 connectable to one more local or remote computer processors configured to sample or analyze ambient air and make an assessment of contaminants or infectious agents present in the ambient air. In one or more arrangements, the analysis and determination of specific agents within the ambient air triggers an alert to the wearer of the mask 202. For example, upon determining a high concentration of pollutants, a processor integral (with associated elements such as memory, input/output, and power) or remote to the mask sends an audio alert to a wearer informing them of the particulate level. Where the processor is integral to the mask, in one arrangement, the processor is configured to communicate with a wireless communication device (such as a smartphone) and provide an application executing on the wireless communication device with the data gathered by the sensors of the mask. In another arrangement, the mask is configured to communicate with a database or data storage device or appliance to record and update a central repository with information about the ambient air quality. In a further implementation, the mask is equipped with one or more cameras 680.

A GPS unit, in one arrangement, is also incorporated or integral to the mask and communicates with one or more processors to provide location data and to transmit location data to a user display or to a remote database.

In a further embodiment, the sensors are integral to the filter modules and are designed to communicate via RF frequencies with one or more processors.

In a particular embodiment, the user mask 202 is equipped with one or more outlet valves configured to expel inhaled air back to the surroundings. In a particular embodiment, the outlet valves are operable by positive or negative pressure valves, such as spring or diaphragm actuated devices such that upon exhalation the valves open and allow air back into the environment. In another arrangement one or more sensors are connected to an electronically activated valve and cause the valve to open in response to measured biometric conditions, such as chest movement or detected exhalation.

In one or more embodiments, the air purifier device described is configured to generate a positive pressure within the mask so as to prevent the infiltration of biological, chemical or radiological elements into the interior space of the mask.

Figure 4:
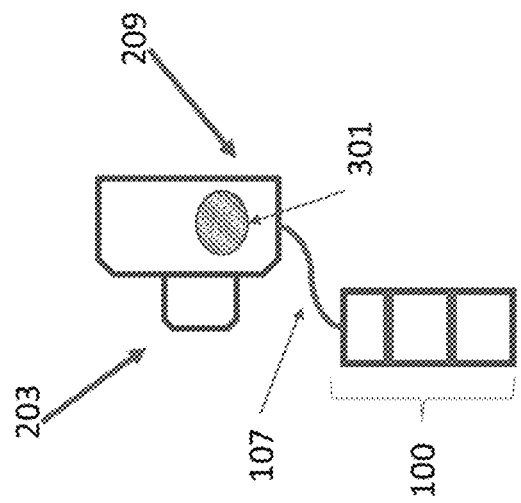
FIG. 4 is an illustrative side view of one of the embodiments.

The outlet valve in one or more configurations directs the expelled air to filtering attachment 203. In a particular configuration, the filtering attachment is directly affixed to the user mask 202 as shown in FIG. 4. The filtering attachment includes one or more filtering elements (not shown). One filtering element is a HEPA filter designed to filter out microorganisms from the air expelled by the user. In a further arrangement, the filtering elements are connectable or stackable such that air that passes through a first filter is then passed though a second, and subsequent filters. In one arrangement, a filtering element is a UV filter element, or other radiation delivering filter that is designed to deliver radiation to the air that has been expelled by the user.

In a particular arrangement, the air filter element includes an electro-static, humidifier, dehumidifier, or other filtering technology to process air that has been expelled by the user. For example, one or more filter elements are negative ion generators, such as those described in CN201510320872 and CN201510320874 herein incorporated by reference in its entirety.

Furthermore, prior to exiting to the ambient air, the expelled air (including air that has been filtered) is analyzed by one or more sensors arranged to analyze the air expelled.

The outlet vent is, in one arrangement, connected to the expelled air filters via a conduit or hose. In this configuration the wearer can pipe or direct the expelled air to a series of filters that are affixed to the wearer or are otherwise remote to the wearer.

The mask 209 can include or incorporate a pair of detachable goggles 670 that are configured to fit over the eyes of the user. In one or more arrangements, the goggles 670 are contoured so as to form a tight seal with the mask 209 but not exchange air between the volume enclosed by the goggles 670 and the volume of air enclosed by the mask. In yet a further arrangement, the goggles 670 include one or more visual display elements, such as a heads-up display, transparent display, monocle, or other display device that is configured to provide visual information to the user. In one particular configuration, the display is configured to provide visual indications as to the ambient air quality or presence of specific or general contamination levels. For example, the goggles 670 are equipped with one or more processors configured to receive data from the processor integral to the mask 209, or from the sensors integral to the mask. In one configuration, the goggles are equipped with one or more cameras to provide a field of view to the user though a display positioned in front of the eyes of the user.

Furthermore, the sensors configured to analyze the expelled air are further configured to provide information to the processor(s), such as the processor of the goggles, and indicate the presence of contaminates within the expelled air of the user. In this configuration, the sensors are configured to evaluate the presence of chemicals, microorganisms, compounds or other indicators of the health of the wearer. In one or more non-limiting embodiments, the sensors integral to the mask can include one or more of the following properties, procedures, requisite hardware and software necessary to effectuate: Gas chromatography-mass spectrometry; GC-MS Proton transfer reaction mass spectrometry PTR-MS and PTR-TOF; selected ion flow tube mass spectrometry SIFT-MS; Ion mobility spectrometry (IMS); Fourier transform infrared spectroscopy FTIR; Laser spectrometry Spectroscopy; Chemical sensors or Electronic noses. The described sensor may implement one or more of the following: metal-oxide-semiconductor (MOSFET) devices—e.g. a transistor used for amplifying or switching electronic signals. In this arrangement, each additional measured particulate will directly affect the transistor in a unique way, producing a change in the MOSFET signal that can then be interpreted by pattern recognition computer systems, such as ones integrated into the mask of the preset device and determine the particular presence of one or more contaminants. Sensors in alternative embodiments further include organic polymers that conduct electricity; polymer composites or a further combination of non-conducting polymers with the addition of conducting material such as carbon black; quartz crystal microbalance sensor utilizing the change in frequency of a quartz crystal resonator to sense the presence of compounds within the air and/or surface acoustic wave (SAW) devices that utilize the modulation of surface acoustic waves to sense a physical phenomenon, such as the presence of various compounds.

In a particular embodiment, each of the modules connected to the common power interface generate a signal or signature receivable by the processor 400. In one or more arrangements, the processor 400 is also connected to the common power interface and is integral to the air purifier device. Here, each module connected to the common power interface broadcasts a signature (such as through a DC based powerline communication, Wifi, Bluetooth, or near field RF communication) that is received by the processor 400. The signals generated by each module include at least a standardized functionality (e.g. filter, humidifier). Additional information can be sent detailing the make, model number, specific purpose, or other elements of interest regarding the module. In a further arrangement, the processor 400 stores the module signature data in one or more local or remote storage locations.

In a particular embodiment, the processor 400 is configured to evaluate through the one or more connectable sensors and filter modules if the present ambient environment is toxic or contaminated. When toxins are detected, the processor 400 is configured by one or more software modules to use the signature of each filter to determine if one or more filters are sufficient to purify the ambient air. By way of non-limiting example, where one or more sensors detects a hazard (e.g. airborne toxin), the processor 400 evaluates the toxin against a stored or accessible list (stored locally or accessible on or through a network) of agents that can be filtered by the one or more filter or conditioning modules. Where the present filters are unsuited to filtering the specific toxin, an alert or alarm is raised indicating that the level of protection is inadequate.

Figure 2:
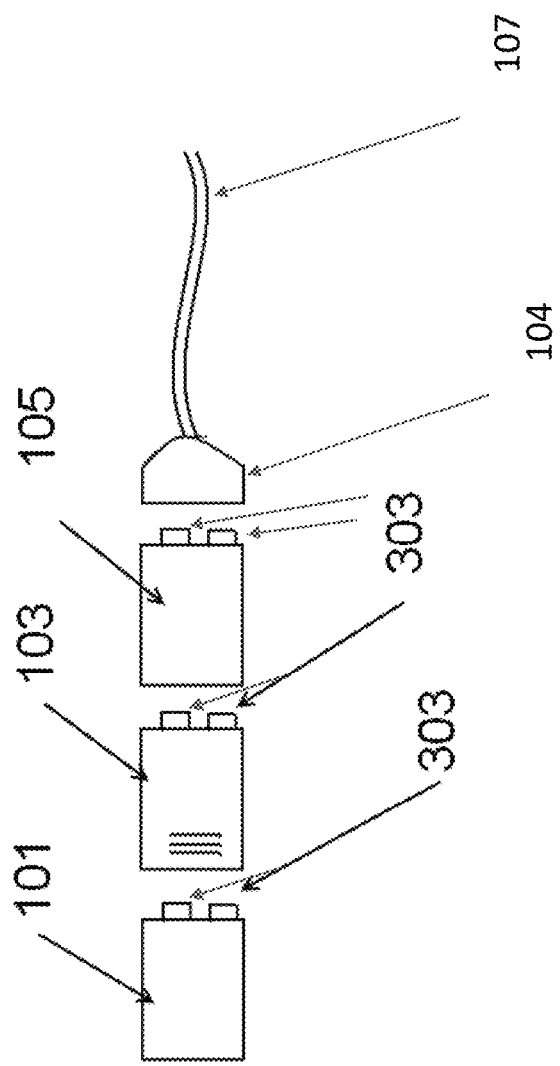
FIG. 2 is an exploded view of an embodiment of the invention.

As described above, the modules of the present device are configured to fit together with one another. Specifically, each module can be combined with other modules so that the electrical and air flow connections can be passed from one module to the next depending on the arrangement of the modules. As depicted in FIG. 2, the power module 101 connects to the air compression module 103 by connection sockets or plugs 303. The connection sockets 303 are equipped with electrical connectors configured to mate with sockets (not shown) located on one end of the air compression module 103. These sockets provide both electrical connections, but also physically connect the modules into a single piece. Additionally, electricity as well as compressed air can be passed to the next module through similarly designed connection sockets 303. In the depicted device the filtering module is connected. In the event that a filtering module is not necessary, the compression cone and hose 107 is fitted to the top most module and is designed to ground the electrical connection and direct the compressed air. In those embodiments where the one or more filtering modules are present, the compression cone and hose 107 is simply secured to the output of the last filter.

Figure 3:
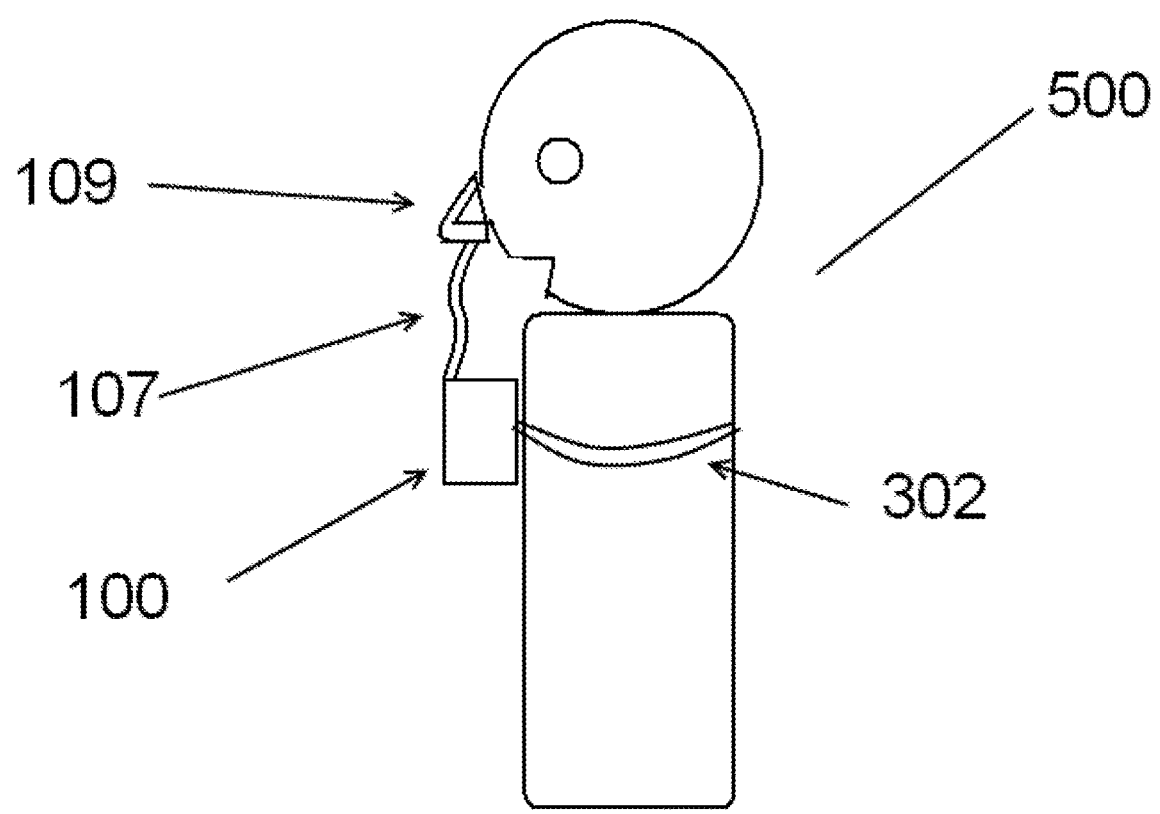
FIG. 3 is an illustrative side view of one of the embodiments.

As depicted in FIG. 3, the device described can be secured to the user 500 by means of a harness or belt 302. The belt or harness can be used to secure both the device when in operation, and also function as a storage unit for when the device is not in use, but is being carried. Additionally, the belt has portions or pouches for the storage of additional filter modules, additional power modules or other elements not herein described.

While the modules herein described are an embodiment of the device as depicted in the Figures, those skilled in the art would recognize the additional modules that could be stacked on the device in question. For example, in a non-depicted embodiment, an additional UV filter is added to the filtering stage. A humidifier module can be added in addition or in alternative to the modules already provided. In both these embodiments, the power module provides sufficient electrical power to provide proper functioning of the modules.

In the alternative arrangement of elements, the portable air purification apparatus is equipped with a second air compression module, wherein the second air compression module provides accelerated and pressurized air stream to the first air compression module.

In an additional alternative arrangement of elements, the portable air purification apparatus is also equipped with an oral cavity mask configured to connect to the filtering module, this could be a separate filtering device from those envisioned as part of the apparatus. In this arrangement, the oral cavity mask is configured to connect to an exhaust outlet. In an alternative arrangement, the power module is a battery pack, alternating current power supply or direct current power supply. The power supply can be computer controlled so as to be on a timer, or respond to environmental conditions and factors.

The filter module can be selectively engageable, that is the filtering functions themselves can be selectively engaged by a user manually, or via a pre-programmed routine stored within the memory of a computer. For example, ionizing radiation inserts integral to a filter module are selectively engaged for specific events or situations. Other inserts for the filter modules are envisioned.

Figure 5:
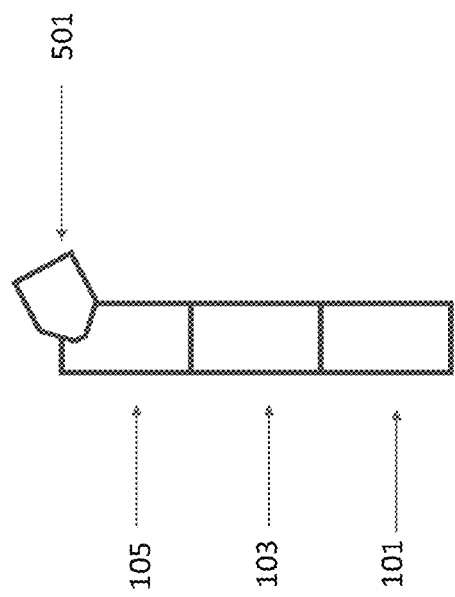
FIG. 5 is an illustrative side view of one of the embodiments of the present invention.

In a further embodiment, the air purifier described eliminates the need of a mask and instead direct air to the face of the user. In this arrangement, as provided in FIG. 5, the purifier filters ambient air using the power module, the compressor and at least one filtering module. The air is then sent to an accelerator 501 to accelerate the air to the face of the user. The accelerator can be a fan or other device configured to compress and send the filtered air to the user. Alternatively, the accelerator can use laminar flow, such as though the use of, planes, foils or other structures to generate an air curtain between the air purifier and the user to prevent the intrusion of contaminates into the user's air stream. In one or more embodiments, the mask-less configuration is secured to a user through a strap, lanyard, harness or other device that allows the accelerator to be positioned so as to direct the purified air stream to the face of the user. For example, the angle and orientation of the accelerator 501 is changeable based on the user's anatomy and physical characteristics.

In a further embodiment of the air purification apparatus described, an oxygen generation module is provided. The air or oxygenation module provides a source of clean air or oxygen to the user independent of filters or other mechanisms used to purify air. For example, in instances where the ambient air can not be filtered, or the filters currently equipped with the air filter apparatus are not sufficient to purify the air to an acceptable level, the oxygenation module provides a source of purified air for use by the wearer. In one configuration, the oxygenation module is a container of pressurized oxygen or air that is equipped with one or more control valves that selectively permit or restrict the flow of air to the air compressor module.

For example, in an arrangement where one or more sensors detects the presence of an airborne toxin that the engaged filters are incapable of filtering, the processor 105 causes the one or more control valves to operate and provide stored oxygen to the user. In this arrangement, the air compression module is also configured with a selectively engageable inlet. Thus, the mask becomes an environment where air or oxygen is provided from only a stored source and the exhaled air is permitted to exit the mask due to positive pressure.

Figure 6:
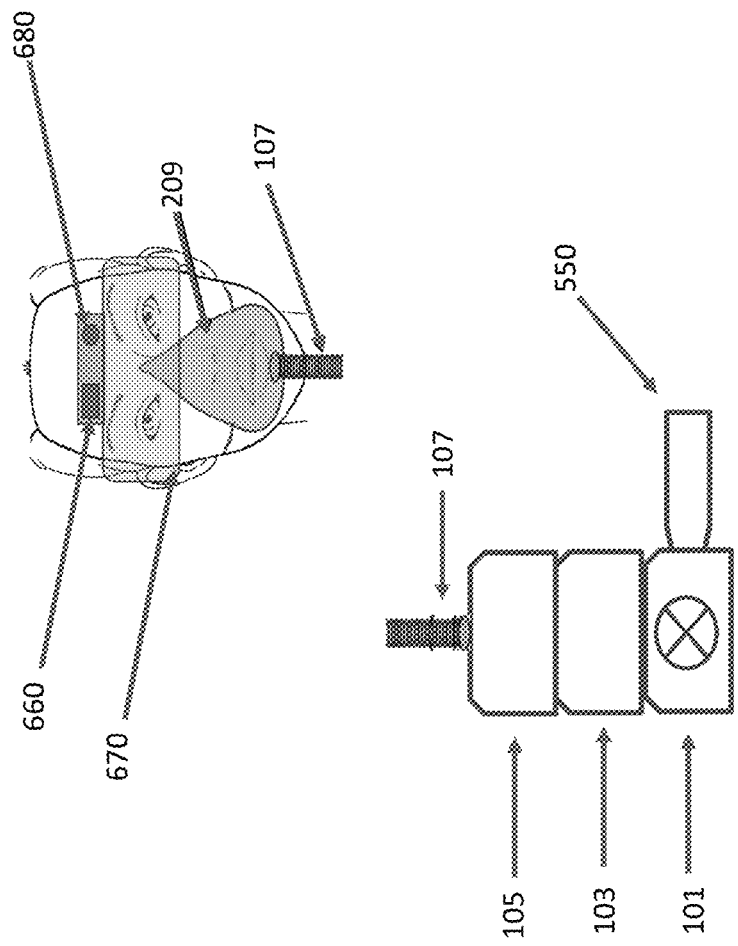
FIG. 6 is a diagram view of one of the embodiments of the present invention.

In one particular arrangement, the air or oxygen is supplied via a pressurized air or oxygen canister. The oxygen canister is, in one configuration, a standard sized oxygen tank equipped with one or more hoses or conduits to connect or transfer air or oxygen to the air compression module 103. In this arrangement, a tank interface module 550 is connectable to the air compressor so as to supply contaminate free air to the user, as shown in FIG. 6.

In an alternative arrangement, an oxygen repository module is connectable to the air purifier apparatus. In one non-limiting arrangement the oxygen repository module contains an amount of an oxygen sequestration compound. For example, in one arrangement the oxygen sequestration compound is 2-aminoterephthalato-linked deoxy system, [{(bpbp)Co2II(NO3)}2(NH2bdc)](NO3)2·2H$_2$O (bpbp-=2, 6-bis(N,N-bis(2-pyridylmethyl)aminomethyl)-4-tert-butylphenolato, NH2bdc2-=2-amino-1,4-benzenedicarboxylato or a nitrate salt thereof as provided in Sundberg, Jonas; Cameron, Lisa J.; Southon, Peter D.; Kepert, Cameron J.; McKenzie, Christine J. (2014). "Oxygen chemisorption/desorption in a reversible single-crystal-to-single-crystal transformation" Chem. Sci., 2014,5, 4017-4025; herein incorporated by reference in its entirety. In an alternative arrangement the sequestration compound is Tetramethylammonium ozonide ((CH3)4NO3).

Figure 7:
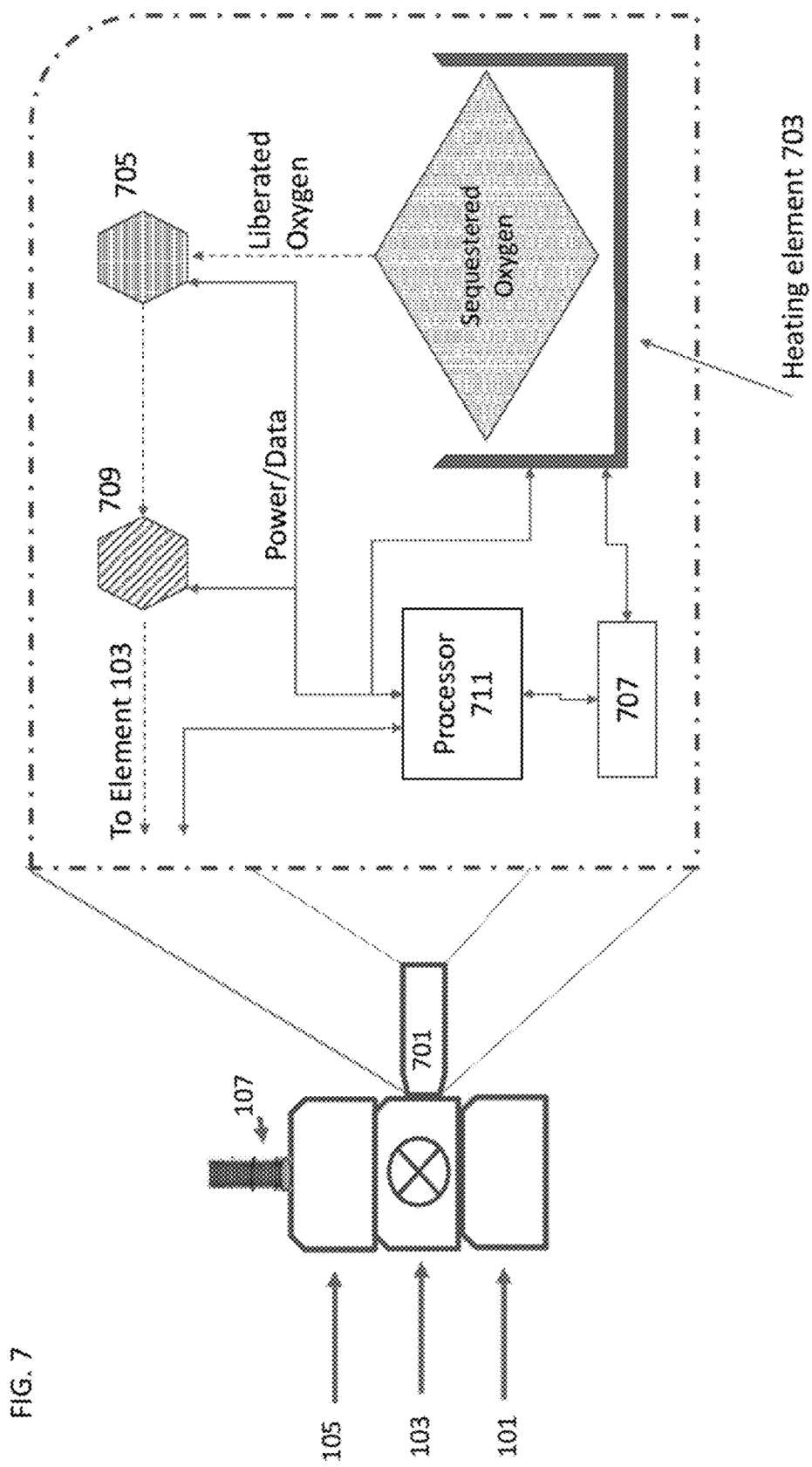
FIG. 7 is an FIG. 9 is an illustrative view of the components of the oxygen generation module according to one embodiment.

In a particular configuration, as shown in FIG. 7, one or more oxygen releasing devices 701 are configured to induce the oxygen sequestration compound to release oxygen. For instance, the air purifier device 100 includes one or more oxygen releasing devices that each contain one or more addressable or controllable heating elements 703 that are configured to heat the oxygen sequestration compound until oxygen is released from the compound. In a particular configuration, the oxygen releasing devices 701 is connectable to the common power and air interface of the air purifier device 100. Here, the processor 105 mediates the functioning of the heating elements to maintain a steady stream of generated uncontaminated oxygen. For example, the oxygen releasing devices 701 also includes temperature sensors 705, backup power supplies 707, oxygen sensors 709, and one or more integrated control processors 711 configured to communicate with the processor 130 or 400 so as to maintain a steady stream of oxygen to the user.

In another arrangement, the oxygen repository module includes a selectable charging port that permits ambient air to come in contact with the oxygen sequestration compound when the compound has been depleted of oxygen. In this arrangement, the oxygen repository module is configured to both store and release oxygen into the air compressor for further use by the air purifier device.

In one arrangement, the oxygen sequestration module includes between 0.1 and 10 liters of sequestration compound.

In a further arrangement, the oxygen repository module utilizes pressure swing absorption devices, chemical oxygen generators, oxygen candles or the components of self contained self rescue devices, such as those using potassium superoxide.

In one or more arrangements, the air purifier is a portable device or collection of devices designed to provide clean, filtered or otherwise processed air to users requiring protection from air pollution, including chemical, radioactive, airborne bacteria, molds, fungus, and virus particulates and particles. Those possessing an ordinary level of skill in the art will appreciate the strategic product benefits of the present device, including its automatic safety features, ease of use, and low-cost. The present invention further utilizing new technologies including nano-manufacturing (such as nanoscale filters, controls, material and or devices) that allow the described device and systems to miniaturize the micro computer, mini air pumps, required sensors and devices that will be made consumer friendly and useful in possible joint ventures with third party manufactures, providers and companies.

It should be understood that various combination, alternatives and modifications of the present invention could be devised by those skilled in the art. The present invention is intended to embrace all such alternatives, modifications and variances that fall within the scope of the appended claims.

In a non-limiting example, the processor 130 and remote computer 600 are commercially available or custom built computers equipped with a one or more processors, graphical processing units, field programmable gate arrays, RAM and ROM memory, network interface adaptors and one or more input or output devices. In a further embodiment, the processor 130 or computer 600 is computer server or collection of computer servers, each server configured to store, access, process, distribute or transmit data between one another and other computers or devices accessible or connectable therewith. In still a further embodiment, processor 130 or computer 600 is a hosted server, virtual machine, or other collection of software modules or programs that are interrelated and hosted in a remote accessible storage device (e.g. cloud storage and hosting implementation) that allows for dynamically allocated additional processors, hardware or other resources on an "as-need" or elastic need basis. In a further embodiment, the processor is configured to implement elastic load balancing algorithms to harness remote computing capacity or functionality to enable the system to handle computationally or otherwise resource intensive actions and procedures.

In a particular arrangement, the processor or computers referenced herein are desktop or workstation computers using commercially available operating system, e.g. WINDOWS®, OSX®, UNIX™ or LINUX™ based implementation. In a further configuration, the processor or computer is a portable computing device such as an Apple IPad/IPhone® or Android® device or other commercially available mobile electronic device configured to have access to or implement remote hardware as necessary to carry out the functions described. In other embodiments, the processor or computer includes custom or non-standard hardware configurations. For instance, the processor or is a one or more micro-computer(s) operating alone or in concert within a collection of such devices, network(s), or array of other micro-computing elements, computer-on-chip(s), prototyping devices, "hobby" computing elements, home entertainment consoles and/or other hardware.

While the invention has been particularly shown and described with reference to a preferred embodiment thereof, it will be understood by those skilled in the art that various changes in form and details may be made therein without departing from the spirit and scope of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter of the present invention have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Publications and references to known registered marks representing various systems are cited throughout this application, the disclosures of which are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

The above descriptions of embodiments of the present invention are not intended to be exhaustive or to limit the systems and methods described to the precise form disclosed. While specific embodiments of, and examples for, the apparatus are described herein for illustrative purposes, various equivalent modifications are possible within the scope of other articles and methods, as those skilled in the relevant art will recognize. The teachings of articles and methods provided herein can be applied to other devices and arrangements, not only for the apparatus and methods described above.

The elements and acts of the various embodiments described above can be combined to provide further embodiments. These and other changes can be made to the apparatus and methods in light of the above detailed description.

What is claimed is:

1. A portable air purification apparatus comprising:
a power module;
a first air compression module having an oxygen inlet port and an air inlet port and an outlet port;
one or more processors configured by code executing therein, two or more selectable activation state filter modules, each having an inlet port and an outlet port and one or more filtering elements disposed between the inlet port and outlet port, wherein a first one of the two or more selectable activation state filter modules is configured to receive a stream of compressed air from the outlet port of the first air compression module at the associated inlet port thereof and pass the stream of compressed air to a corresponding inlet port of a second one of the two or more selectable state activation filter modules, and wherein each of the two or more selectable state activation filter modules are configured to receive electrical energy from an electrical energy port and pass at least a portion of the received electrical energy to a filter energy outlet port, wherein an activation state of the two or more selectable filtering modules is triggered in response to a filtering signal received from one or more processors;

an oxygen sequestration module, wherein the oxygen sequestration module includes an oxygen sequestration compound, tetramethylammonium ozonide, and an oxygen liberation device, the oxygen liberation device selectably activated by an oxygen generation signal from the one or more processors configured to receive a value corresponding to an amount of oxygen in an ambient environment of the wearer so as to provide contained oxygen from the oxygen sequestration module to the oxygen inlet port of the air compression module; the oxygen sequestration module further incorporating a heating element, an oxygen sensor, and a temperature sensor, wherein the heating element is selectively activated to heat the oxygen sequestration compound in response to the oxygen generation signal from the one or more processors based on the amount of oxygen measured by the oxygen sensor such that an amount of the contained oxygen is produced by the oxygen sequestration module; and a mask configured to be fitted over the nose and mouth of a wearer and configured to receive the stream of compressed air that has passed through the two or more selectable activation state filtering modules.

2. The portable air purification apparatus of claim 1, further comprising,
a plurality of air quality sensors integral to the mask and configured to sample ambient air, the sensors further configured to communicate with the one or more processors, wherein upon detecting one of a pre-determined plurality of air contaminants, the sensors are configured to send a sensor signal to the one or more processors; wherein upon receipt of the sensor signal by the one or more processors, the one or more processors is configured to generate the filtering signal to change the selectable activation state filtering module.

3. The portable air purification apparatus of claim 2, wherein the one or more processors is a remote computing device.

4. The portable air purification apparatus of claim 3, wherein the processor is configured to communicate with the plurality of sensors using radio frequencies.

5. The portable air purification apparatus of claim 2, wherein the processor is further configured to alert the wearer to air quality conditions sensed.

6. The portable air purification apparatus of claim 5, further comprising a display device, wherein the one or more processors is configured to provide a visual indicator to the display device to indicate air quality conditions determined.

7. The portable air purification apparatus of claim 6, wherein the display device is a display configured to be mounted to the wearer's head.

8. The portable air purification apparatus of claim 7, wherein the display device is equipped with one or more cameras, wherein the one or more cameras are configured to provide images to the wearer through a screen positioned in front of the eyes of the wearer.

9. The portable air purification apparatus of claim 2, further comprising,
one or more outlet valves integral to the mask configured to permit the stream of compressed air to move from a space between the mask and the wearer to an external space outside the mask; and one or more filters configured to communicate with the one or more outlet valves and configured to filter exhaled air prior to passing the exhaled air to the ambient environment.

10. The apparatus of claim 2, wherein upon receipt of the sensor signal from at least one of the air quality sensors, the processor is configured to change the activation state of at least one of the two or more selectable activation state filter modules where the processor determines that at least one of the two or more selectable activation state filter modules is configured to remove at least one of the predetermined plurality of contaminants detected by the air quality sensor.

* * * * *